United States Patent
Lu et al.

(10) Patent No.: US 11,545,633 B2
(45) Date of Patent: Jan. 3, 2023

(54) 3,7-BIS(2-OXOINDOLIN-3-YLIDENE)BENZO[1,2-B:4,5-B']DIFURAN-2,6-DIONE DICYANIDE-BASED MATERIALS AND USES THEREOF IN ORGANIC ELECTRONIC DEVICES

(71) Applicants: NATIONAL RESEARCH COUNCIL OF CANADA, Ottawa (CA); Yuning Li, Kitchener (CA); Jesse Quinn, Toronto (CA)

(72) Inventors: Jianping Lu, Ottawa (CA); Afshin Dadvand, Montreal (CA); Mark Bortolus, Hamilton (CA); Salima Alem, Ottawa (CA); Ye Tao, Ottawa (CA); Yuning Li, Kitchener (CA); Jesse Quinn, Toronto (CA)

(73) Assignees: NATIONAL RESEARCH COUNCIL OF CANADA, Ottawa (CA); Yuning Li, Kitchener (CA); Jesse Quinn, Toronto (CA)

( * ) Notice: Subject to any disclaimer, the term of this patent is extended or adjusted under 35 U.S.C. 154(b) by 85 days.

(21) Appl. No.: 16/980,609

(22) PCT Filed: Mar. 13, 2019

(86) PCT No.: PCT/IB2019/052046
§ 371 (c)(1),
(2) Date: Sep. 14, 2020

(87) PCT Pub. No.: WO2019/175804
PCT Pub. Date: Sep. 19, 2019

(65) Prior Publication Data
US 2021/0013424 A1   Jan. 14, 2021

Related U.S. Application Data

(60) Provisional application No. 62/642,630, filed on Mar. 14, 2018.

(51) Int. Cl.
*H01L 51/00* (2006.01)
*C07D 493/04* (2006.01)
(Continued)

(52) U.S. Cl.
CPC ........ *H01L 51/0072* (2013.01); *C07D 493/04* (2013.01); *H01L 51/0073* (2013.01); *H01L 51/0558* (2013.01); *H01L 51/42* (2013.01)

(58) Field of Classification Search
CPC .............................. G02B 5/22; H01L 51/0072
See application file for complete search history.

(56) References Cited

U.S. PATENT DOCUMENTS

2015/0147493 A1   5/2015   Ruch et al.
2015/0295179 A1   10/2015  Li

FOREIGN PATENT DOCUMENTS

| CN | 104761563 A | * 7/2015 | ........... C07D 493/04 |
| CN | 104761563 A1 | 7/2015 | |
| JP | 2015185096 A | * 10/2015 | ............... G02B 5/22 |

OTHER PUBLICATIONS

II. Kang,etal, Record high hole mobility in polymer semiconductors via side-chain engineering, J. Am. Chem. Soc. 2013, 135, 14896.

(Continued)

*Primary Examiner* — Khanh T Nguyen
(74) *Attorney, Agent, or Firm* — Aird & McBurney LP (57) ABSTRACT

The development of air-stable unipolar n-type semiconductors with good solubility in organic solvents at room temperature remains a critical issue in the field of organic electronics. Moreover, most of the existing semiconducting materials exhibit LUMO energy levels higher than −4.0 eV, making electron transport sensitive to both moisture and oxygen. Bis(2-oxoindolin-3-ylidene)benzodifurandione dicyanide or derivatives thereof are disclosed herein. More specifically, bis(2-oxoindolin-3-ylidene)benzodifurandione (Continued)

dicyanide or derivatives thereof for use in organic electronics are disclosed. A process for the preparation of bis(2-oxoindolin-3-ylidene)benzodifurandione dicyanide and derivatives is also disclosed. The bis(2-oxoindolin-3-ylidene)benzodifurandione dicyanide or derivatives thereof are characterized by high electron mobilities and are suitable for use as n-type semiconductors in organic electronics.

14 Claims, 4 Drawing Sheets

(51) Int. Cl.
　　　H01L 51/05　　　(2006.01)
　　　H01L 51/42　　　(2006.01)

(56) References Cited

OTHER PUBLICATIONS

Y. Li, P. Sonar, L. Murphya, W. Honga, Energy Environ. Sci. 2013, 6, 1684.
H. Tseng et al, High-mobility field-effect transistors fabricated with macroscopic aligned semiconducting polymers, Adv. Mater. 2014, 26, 2993.
Y. Yuan, G. Giri, A. L. Ayzner, A. P. Zoombelt, S. C. B. Mannsfeld, J. Chen, D. Nordlund, M. F. Toney, J. Huang, Z. Bao, Nature Commun. 2014, 5, 3005.
J. Li, Y. Zhao, H. Tan, Y. Guo, C. Di, G. Yu, Y. Liu, M. Lin, S. Lim, Y. Zhou, H, Su, B. Ong, Sci. Rep. 2012, 2, 754.
X. Zhan, A. Facchetti, S. Barlow, T. J. Marks, M. A. Ratner, M. R. Wasielewski, S. R. Marder, Adv. Mater. 2011, 23, 268.
T. Lei, X. Xia, J. Wang, C. Liu, J. Pei, J. Am. Chem. Soc. 2014, 136, 2135.
J. Dou, Y. Zheng, Z. Yao, Z. Yu, T. Lei, X. Shen, X. Luo, J. Sun, S. Zhang, Y. Ding, G. Han, Y. Yi, J. Wang, J. Pei, J. Am. Chem. Soc. 2015, 137, 15947-15956.
F. Zhang, Y. Hu, T. Schuettfort, C. Di, X. Gao, C. McNeill, L. Thomsen, S. Mannsfeld, W. Yuan, H. Sirringhaus, D. Zhu, Critical Role of Alkyl Chain Branching of Organic Thin-Film Transistors With Mobility of up to 3.50 CM2V1S1N, J. Am. Chem. Soc. 2013, 135, 2338.
H.-Y. Chen, J. Hou, S. Zhang, Y. Liang, G. Yang, Y. Yang, L. Yu, Y. Wu and G. Li, Nature Photon., 2009, 3, 649.
Z. Li, J. Lu, S. Tse, J. Zhou, X. Du, Y. Tao, J. Ding, J. Mater. Chem., 2011, 21, 3226-3233.
S. Alem, S. Wakim, J. Lu, G. Robertson, J. Ding, Y. Tao, ACS Appl. Mater. Interfaces, 2012, 4, 2993-2998.
T. Lei, J. Dou, J. Pei, Adv. Mater. 2012, 24, 6457.

J. Mei, D. H. Kim, A. L. Ayzner, M. F. Toney, Z. Bao, et al., J. Am. Chem. Soc. 2011, 133, 20130.
Lei, T et al, Journal of the American Chemical Society, Jan. 15, 2014 , vol. 136(5), pp. 2135-2141.
Quinn, J.T.E. et al, Recent Progress in the Development of N-Type Organic Semiconductors for Organic Field Effect Transistors, Journal of Materials Chemistry C, Aug. 1, 2017, vol. 5(34), pp. 8654-8681.
He, Y. et al., Branched Alkyl Ester Side Chains Rendering Large Polycyclic (3E,7E)-3,7-Bis(2-Oxindolin-3-Lidene)Benzo[1,2-B:4,5-B'}Difuran-2,6(3H,7h)-Dione (IBDF) Based Donor-Acceptor Polymers Solution-Processability for Organic Thin Film Transistors, Polymer Chemistry, Oct. 7, 2015, vol. 6(37), pp. 6689-6697.
Dhar, J. et al., Trends in Molecular Design Strategies for Ambient Stable-N-Channel Organic Field Effect Transistors, Journal of Materials Chemistry C, Jan. 1, 2017, vol. 5(3), pp. 7404-7430.
Dou, J. H. et al., Fine-Tuning Crystal Packing and Charge Transport Properties of BDOPV Derivatices Through Fluorine Substituion. Journal of the American Chemical Society, Nov. 30, 2015 , vol. 137(5), pp. 15947-15956.
Yan, Z. et al., Development of New Building Blocks for Constructing Novel Polymer Semiconductors for Organic Thin Film Transistors., Master of Applied Science, 2013, May 22, 2019.
Atul Goel et al, Vapor-Phase Processable Novel Nonplanar Donor-Acceptor Quaterary1s for Blue-OLEDs#, Organic Letters, 2008.
Jwo-Huei Jou et al, Highly efficient ultra-deep blue organic light-emitting diodes with a wet-and dry-process feasible cyanofluorene acetylene based emitter, Journal of Materials Chemistry C, Issue 10, 2015.
Yan, Z. ET A novel stable (3E,7E)-3,7-bis(2-oxoindolin-3-ylidene)benzo[1,2-b:4,5-b']difuran-2,6(3H,7H)-dione based donor-acceptor polymer semiconductors for n-type organic thin film transistors, Chem Commun (Camb), 8;49(36):3790-2, 2013.
Guobing Zhang et al, A bis(2-oxoindolin-3-ylidene)-benzodifurandione containing copolymer for high-mobility ambipolar transistors, Chem. Commun. 2014.
Guobing Zhang et al, Bis(2-oxoindolin-3-ylidene)-benzodifurandione containinbased D-A polymers for high-performance n-channel transistors, Royal Society of Chemistry, Polym. Chem. 2015.
Guobing Zhang et al, Bis(2-oxo-7-azaindolin-3-ylidene)benzodifurandione-based donor-acceptor polymers for high-performance n-type field-effect transistors, Polymer Chemistry, 2017—Abstract.
Xu Zhou et al, Balanced ambipolar organic thin-film transistors operated under ambient conditions: Role of the donor moiety in BDOPV-Based conjugated copolymers, Chemistry of Materials, 2015.
Min Zhu et al, Enhnaced near-infrared photoresponse of organic phototransistors based on single-component donor-acceptor conjugated polymer nanowires, Nanoscale, 2016, 8, 7738, 2016.
International Search Report and Written Opinion dated Jun. 18, 2019.

* cited by examiner

3,7-BIS(2-OXOINDOLIN-3-YLIDENE)BENZO[1,2-B:4,5-B']DIFURAN-2,6-DIONE DICYANIDE-BASED MATERIALS AND USES THEREOF IN ORGANIC ELECTRONIC DEVICES

CROSS-REFERENCE TO RELATED APPLICATIONS

This application is a national phase entry of International Patent Application PCT/IB2019/052046 filed Mar. 13, 2019, which claims the benefit of United States Provisional Patent Application Ser. No. 62/642,630 filed Mar. 14, 2018.

FIELD

The present disclosure broadly relates to electroactive and photoactive materials. More specifically but not exclusively, the present disclosure relates to 3,7-bis(2-oxoindolin-3-ylidene)benzo[1,2-b:4,5-b']difuran-2,6-dione dicyanide-based electroactive and photoactive materials. The present disclosure also relates to a process for the preparation of 3,7-bis(2-oxoindolin-3-ylidene)benzo[1,2-b:4,5-b']difuran-2,6-dione dicyanide and derivatives thereof. Moreover, the present disclosure relates to the use of 3,7-bis(2-oxoindolin-3-ylidene)benzo[1,2-b:4,5-b']difuran-2,6-dione dicyanide-based materials in organic electronics.

BACKGROUND

Organic electronic devices have been intensely investigated in both academia and industry over the last two decades because of their promising potential for broad commercial applications, non-limiting examples of which include light-emitting diodes, field effect transistors, organic solar cells and chemo-/biosensors. Moreover, organic electronics can be fabricated on plastic substrates to enable light weight, flexible and even wearable electronic devices. Such devices typically comprise organic semiconducting materials which are used as thin active layers.

Tuning of the physical and electro-optical properties of conjugated polymers through chemical modification of their backbone has led to a wide array of promising materials for organic electronics applications. Indeed, with polymer solar cells (PSC) with power conversion efficiencies (PCE) exceeding 10%, organic field effect transistors (OFETs) with hole mobilities up to 20 $cm^2\ V^{-1}\ s^{-1}$ and electron mobilities as high as 7.0 $cm^2\ V^{-1}\ s^{-1}$, conjugated polymers now show performances suitable for commercial applications.

Significant progress has been made in p-type materials, which have demonstrated high hole mobilities (>10 $cm^2\ V^{-1}\ s^{-1}$) well beyond the mobility of amorphous silicon.[1-5] However, major challenges remain in the development of solution-processed, air-stable electron-transporting (n-type) organic materials. Indeed, in order to realize air-stable electron transport in organic semiconductors, a low LUMO energy level below −4.1 eV is required.[6] However, most of the semiconducting polymers reported so far exhibit LUMO energy levels higher than −4.0 eV, making electron transport sensitive to both moisture and oxygen. To that effect, one of the best commercially available n-type materials P(NDI2OD-T2) (available from Polyera) exhibits good electron mobility above 0.1 $cm^2\ V^{-1}\ s^{-1}$ in bottom-contact top-gated transistors. However, in bottom-contact bottom-gated transistors, its electron mobility decreased to 0.01 $cm^2\ V^{-1}\ s^{-1}$. Largely in view of its relatively high-lying LUMO energy level (−3.9 eV), the unprotected device lost its performance in just a few hours following its exposure to air.

Several electron-deficient building blocks with low-lying LUMO energy levels demonstrating promising n-type performance in air, such as fluorinated benzodifurandione-based oligo(p-phenylene vinylene) (BDOPV) and naphthalene diimide fused with 2-(1,3-dithiol-2-ylidene) malononitrile, have recently been recorded.[7-9] However, the solubility of these materials was not good enough for inkjet printing. The development of air-stable unipolar n-type semiconductors with good solubility in organic solvents at room temperature remains a critical issue in the field of organic electronics in view of n-type transistors being indispensable components in the manufacture of low-power-consumption complementary metal-oxide semiconductor (CMOS) type integrated circuits.

In recent years, bis(2-oxoindolin-3-ylidene)benzodifurandione (BOIBDD) has emerged as an important building block for the synthesis of high-mobility organic semiconductors because of its unique coplanar structure, with its backbone conformation locked by intramolecular hydrogen bonding.[10] Moreover, fluorine substitution has been widely used to modulate the energy levels of organic semiconductors due to its strong electron-withdrawing capability.[11-12] Fluorine substitution was shown to lower both the HOMO and LUMO energy levels of BOIBDD derivatives, resulting in materials exhibiting air-stable electron transport.[7-8] The BOIBDD derivative comprising four (4) fluorine atoms was shown to exhibit the best performance. Notwithstanding the results obtained with fluorine substitutions, the synthesis of multi-fluorinated compounds remains complicated and quite costly.

The design and use of solubilizing side chains have gained growing attention in the field of organic electronics because of the impact of such side chains on the solubility as well as on the molecular packing of the resulting materials. The incorporation of specific side chains was reported as influencing both material stability as well as the energy bandgap of the resulting organic semiconductors.[13]

SUMMARY

In an aspect, the present disclosure broadly relates to electroactive and photoactive materials. More specifically but not exclusively, the present disclosure relates to 3,7-bis(2-oxoindolin-3-ylidene)benzo[1,2-b:4,5-b']difuran-2,6-dione dicyanide-based electroactive and photoactive materials. The present disclosure also relates to a process for the preparation of 3,7-bis(2-oxoindolin-3-ylidene)benzo[1,2-b:4,5-b']difuran-2,6-dione dicyanide and derivatives thereof. Moreover, the present disclosure relates to the use of 3,7-bis(2-oxoindolin-3-ylidene)benzo[1,2-b:4,5-b']difuran-2,6-dione dicyanide-based materials in organic electronics. In an embodiment of the present disclosure, the organic electronics include photovoltaic devices (e.g. solar cells), field effect transistors and light-emitting diodes.

In an aspect, the present disclosure relates to n-type semiconductors. In a further embodiment, the present disclosure relates to air-stable unipolar n-type semiconductors that are soluble in organic solvents. In a further embodiment, the present disclosure relates to n-type semiconductors for use in the manufacture of low-power-consumption complementary metal-oxide semiconductor (CMOS) type integrated circuits. In a further embodiment of the present disclosure, the n-type semiconductors comprise a material including 3,7-bis(2-oxoindolin-3-ylidene)benzo[1,2-b:4,5-b']difuran-2,6-dione dicyanide or derivatives thereof.

In an aspect, the present disclosure relates to electroactive and photoactive materials having high electron mobility. In an embodiment, the present disclosure relates to bis(2-oxoindolin-3-ylidene)benzodifurandione dicyanide and derivatives thereof.

In an aspect, the present disclosure relates to n-type semiconductors having high electron mobility. In an embodiment, the present disclosure relates to bis(2-oxoindolin-3-ylidene)benzodifurandione dicyanide and derivatives thereof.

In an aspect, the present disclosure relates to n-type semiconductors having LUMO energy levels at or below −4.1 eV. In an embodiment, the present disclosure relates to bis(2-oxoindolin-3-ylidene)benzodifurandione dicyanide and derivatives thereof.

In an aspect, the present disclosure relates to bis(2-oxoindolin-3-ylidene)benzodifurandione dicyanide. In a further embodiment, the present disclosure relates to bis(2-oxoindolin-3-ylidene)benzodifurandione dicyanide and derivatives thereof.

In an embodiment, the present disclosure relates to a bis(2-oxoindolin-3-ylidene)benzodifurandione dicyanide derivative of formula (I):

wherein:
X and Y are independently selected from H and F; and
R is H, $C_{1-40}$alkyl, fluorinated $C_{1-40}$alkyl, $C_{2-40}$alkenyl, fluorinated $C_{2-40}$alkenyl, $C_{2-40}$alkynyl, fluorinated $C_{2-40}$alkynyl, $C_{5-40}$aryl, or $C_{5-40}$heteroaryl.

In an embodiment, the present disclosure relates to a bis(2-oxoindolin-3-ylidene)benzodifurandione dicyanide derivative of formula (I):

wherein:
X and Y are independently selected from H and F; and
R is H or $C_{1-40}$alkyl.

In an embodiment, the present disclosure relates to a bis(2-oxoindolin-3-ylidene)benzodifurandione dicyanide derivative of formula (I):

wherein:
X and Y are H; and
R is H or $C_{1-40}$alkyl.

In a particular embodiment, the present disclosure relates to a bis(2-oxoindolin-3-ylidene)benzodifurandione dicyanide derivative consisting of the structure:

In a particular embodiment, the present disclosure relates to a bis(2-oxoindolin-3-ylidene)benzodifurandione dicyanide derivative consisting of the structure:

In an embodiment, the present disclosure relates to an n-type organic semiconductor material, layer or component, comprising a bis(2-oxoindolin-3-ylidene)benzodifurandione dicyanide or derivatives thereof in accordance with the present disclosure.

In an embodiment, the present disclosure relates to an electronic device comprising a bis(2-oxoindolin-3-ylidene)benzodifurandione dicyanide or derivatives thereof in accordance with the present disclosure. In a particular embodiment of the present disclosure, the electronic device is an organic photovoltaic device, a photodiode or an organic filed effect transistor.

In an embodiment, the present disclosure relates to the use of a bis(2-oxoindolin-3-ylidene)benzodifurandione dicyanide or derivatives thereof in accordance with the present disclosure, as an organic semiconductor material, layer or component.

In an embodiment, the present disclosure relates to the use of a bis(2-oxoindolin-3-ylidene)benzodifurandione dicyanide or derivatives thereof in accordance with the present disclosure, in an electronic device. In a particular embodiment of the present disclosure, the electronic device is an organic photovoltaic device, a photodiode or an organic filed effect transistor.

In an embodiment, the present disclosure relates to a process for preparing bis(2-oxoindolin-3-ylidene)benzodifurandione dicyanide. In a further embodiment, the present disclosure relates to a process for preparing bis(2-oxoindolin-3-ylidene)benzodifurandione dicyanide and derivatives thereof.

In an embodiment, the present disclosure relates to a process for preparing bis(2-oxoindolin-3-ylidene)benzodifurandione dicyanide and derivatives thereof, the process comprising reacting a compound of formula II:

II wherein X and Y are independently selected from H and F; and R is H, $C_{1-40}$alkyl, fluorinated $C_{1-40}$alkyl, $C_{2-40}$alkenyl, fluorinated $C_{2-40}$alkenyl, $C_{2-40}$alkynyl, fluorinated $C_{2-40}$alkynyl, $C_{5-40}$aryl, or $C_{5-40}$heteroaryl; with benzodifurandione. In a further embodiment of the present disclosure, the compound of formula II is prepared by reacting a compound of formula III:

III with a cyanating reagent. In a particular embodiment of the present disclosure, the reaction of the compound of formula (II) with benzodifurandione is a condensation reaction. In a particular embodiment of the present disclosure, the cyanating reagent is CuCN. In a particular embodiment of the present disclosure, the cyanation reaction comprises the use of NMP.

In an embodiment, the present disclosure relates to a process for preparing bis(2-oxoindolin-3-ylidene)benzodifurandione dicyanide and derivatives thereof, the process comprising reacting a compound of formula II:

II wherein X and Y are independently selected from H and F; and R is H or $C_{1-40}$alkyl; with benzodifurandione. In a further embodiment of the present disclosure, the compound of formula II is prepared by reacting a compound of formula III:

III with a cyanating reagent. In a particular embodiment of the present disclosure, the cyanating reagent is CuCN. In a particular embodiment of the present disclosure, the reaction of the compound of formula (II) with benzodifurandione is a condensation reaction. In a particular embodiment of the present disclosure, the cyanation reaction comprises the use of NMP.

In an embodiment, the present disclosure relates to a process for preparing bis(2-oxoindolin-3-ylidene)benzodifurandione dicyanide and derivatives thereof, the process comprising reacting a compound of formula II:

II wherein X and Y are H; and R is H or $C_{1-40}$alkyl; with benzodifurandione. In a further embodiment of the present disclosure, the compound of formula II is prepared by reacting a compound of formula III:

III with a cyanating reagent. In a particular embodiment of the present disclosure, the cyanating reagent is CuCN. In a particular embodiment of the present disclosure, the reaction of the compound of formula (II) with benzodifurandione is a condensation reaction. In a particular embodiment of the present disclosure, the cyanation reaction comprises the use of NMP.

The foregoing and other advantages and features of the present disclosure will become more apparent upon reading of the following non-restrictive description of illustrative embodiments thereof, given by way of example only with reference to the accompanying drawings/figures.

DETAILED DESCRIPTION

Glossary

In order to provide a clear and consistent understanding of the terms used in the present disclosure, a number of definitions are provided below. Moreover, unless defined otherwise, all technical and scientific terms as used herein have the same meaning as commonly understood by one of ordinary skill in the art to which this specification pertains.

The word "a" or "an" when used in conjunction with the term "comprising" in the claims and/or the specification may mean "one", but it is also consistent with the meaning of "one or more", "at least one", and "one or more than one" unless the content clearly dictates otherwise. Similarly, the word "another" may mean at least a second or more unless the content clearly dictates otherwise.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this specification and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±1% of the modified term if this deviation would not negate the meaning of the word it modifies.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The expression "proceed to a sufficient extent" as used herein with reference to the reactions or process steps disclosed herein means that the reactions or process steps proceed to an extent that conversion of the starting material to product is maximized. Conversion may be maximized when greater than about 5, 10, 15, 20, 25, 30, 35, 40, 45, 50, 55, 60, 65, 70, 75, 80, 85, 90, 95 or 99% of the starting material is converted to product.

The term "substituted" as used herein, means that a hydrogen radical of the designated moiety is replaced with the radical of a specified substituent, provided that the substitution results in a stable or chemically feasible compound. Non-limiting examples of substituents include halogen (F, Cl, Br, or I) for example F, cyano, hydroxyl, alkylthiol, alkoxy, carbonyl, alkyl, cycloalkyl, alkenyl, alkynyl, aryl and heteroaryl.

As used herein, the term "alkyl" can be straight-chain or branched. This also applies if they carry substituents or occur as substituents on other residues, for example in alkoxy residues, alkoxycarbonyl residues or arylalkyl residues. Substituted alkyl residues can be substituted in any suitable position. Examples of alkyl residues containing from 1 to 40 carbon atoms are methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, triacontyl, hentriacontyl, dotriacontyl, tritriacontyl, tetratriacontyl, pentatriacontyl, hexatriacontyl, heptatriacontyl, octatriacontyl, nonatriacontyl, tetracontyl, the n-isomers of all these residues, isopropyl, isobutyl, isopentyl, neopentyl, isohexyl, isodecyl, 3-methylpentyl, 2,3,4-trimethylhexyl, sec-butyl, tert-butyl, or tert-pentyl. A specific group of alkyl residues is formed by the residues methyl, ethyl, n-propyl, isopropyl, n-butyl, isobutyl, sec-butyl and tert-butyl.

As used herein, the term "cycloalkyl" is understood as being a carbon-based ring system, non-limiting examples of which include cyclopropyl, cyclobutyl, cyclopentyl and cyclohexyl.

The terms "alkoxy" or "alkyloxy," as used interchangeably herein, represent an alkyl group attached to the parent molecular group through an oxygen atom.

The term "alkylthio" as used herein, represents an alkyl group attached to the parent molecular group through a sulfur atom.

The term "alkenyl," as used herein, represents straight or branched chain groups of, unless otherwise specified, from 2 to 40 carbons, such as, for example, 2 to 20 carbon atoms or 2 to 10 carbon atoms, containing one or more carbon-carbon double bonds and is exemplified by ethenyl, 1-propenyl, 2-propenyl, 2-methyl-1-propenyl, 1-butenyl, 2-butenyl and the like and may be optionally substituted with one, or more substituents.

The term "alkynyl" as used herein, represents straight or branched chain groups of unless otherwise specified, from 2 to 40 carbons, such as, for example, 2 to 20 carbon atoms or 2 to 10 carbon atoms, containing one or more carbon-carbon triple bonds and is exemplified by ethynyl, 1-propynyl, and the like and may be optionally substituted with one or more substituents.

The term "carbonyl" as used herein, represents a C=O group.

As used herein, the term "aryl" is understood as being an aromatic group which is a single ring or multiple rings fused, bridged or linked together and which is optionally substituted. Unless otherwise specified, aryl groups comprise from 5 to 40 carbons, such as, for example, 5 to 20 carbon atoms or 5 to 10 carbon atoms. When formed of multiple rings, at least one of the constituent rings is aromatic. In an embodiment, aryl substituents include phenyl, biphenyl, naphthyl, anthracenyl, indanyl, tetralinyl and fluorenyl groups.

The term "heteroaryl" as used herein embraces fully unsaturated or aromatic heterocyclo groups which are optionally substituted. The heteroaryl groups are either monocyclic, bicyclic, tricyclic or quadracyclic, provided they have a suitable number of atoms, for example from 3 to 40 atoms, and are stable. A bicyclic, tricyclic or quadracyclic heteroaryl group is fused, bridged and/or simply linked via a single bond. Examples of heteroaryl groups include unsaturated 3 to 6-membered heteromonocyclic groups containing an oxygen atom, including, for example, pyranyl, furyl, etc.; unsaturated 3 to 6-membered heteromonocyclic groups containing a sulfur or a selenium atom, including for example, thienyl, selenophenyl, etc.; unsaturated linked 5 or 6-membered heteromonocyclic groups containing 1 to 2 sulfur atoms, including, for example, bithienyl and trithienyl and the like. The term also embraces groups where heterocyclo groups are fused with aryl groups. Examples of such fused bicyclic groups include benzofuranyl, benzothiophenyl, benzopyranyl, benzodioxolyl, and the like.

The term "derivative" as used herein, is understood as being a substance which comprises the same basic carbon skeleton and carbon functionality in its structure as a given compound, but can also bear one or more substituents.

The term "analogue" as used herein, is understood as being a substance similar in structure to another compound but differing in some slight structural detail.

The term "n-type semiconducting material" or "n-type semiconductor" as used herein refers to a semiconducting material having electrons as the majority current carriers. They are therefore electron transporting materials.

The term "p-type semiconducting material" or "p-type semiconductor" as used herein refers to a semiconducting material having holes as the majority current carriers.

The term "field effect mobility" as used herein refers to a measure of the velocity with which charge carriers, for example, holes (or units of positive charge) in the case of a p-type semiconducting material and electrons in the case of an n-type semiconducting material, move through the material under the influence of an electric field.

The term "halogen" or "halo" as used interchangeably herein, represents F, Cl, Br and I.

The term "inert solvent" as used herein refers to any solvent or mixture of solvents in which the reagents in a chemical reaction are substantially soluble, at least to the extent to allow the chemical reaction, and which does not interfere with or inhibit the chemical reaction. The selection of a suitable inert solvent is well within the skill of a person in the art.

In an aspect, the present disclosure relates to cyano-substituted BOIBDD derivatives. In a further aspect, the present disclosure relates to a process for preparing cyano-substituted BOIBDD derivatives. It was surmised that in view of the cyano group being a stronger electron-withdrawing group than a fluorine atom, the incorporation of cyano groups into the BOIBDD core structure could likely further improve the electron transporting performance of this material. To that effect, cyano substitution was carried out in a single step using readily available CuCN as the cyanating reagent.

In an aspect, the present disclosure relates to cyano-substituted BOIBDD derivatives further comprising side chains incorporated onto the oxoindole group. The incorporation of such side chains resulted in more rigid materials exhibiting improved solubility in organic solvents. The increased solubility makes the materials more suitable for solution processing and improves the film-forming properties of the resulting organic semiconductors. In an embodiment of the present disclosure, the side chains are incorporated onto the nitrogen atom of the oxoindole group.

In an aspect, the present disclosure relates to 3,7-bis(2-oxoindolin-3-ylidene)benzo[1,2-b:4,5-b']difuran-2,6-dione dicyanide and derivatives thereof. In a further aspect, the present disclosure relates to the use of 3,7-bis(2-oxoindolin-3-ylidene)benzo[1,2-b:4,5-b']difuran-2,6-dione dicyanide and derivatives thereof in organic electronic devices.

In an aspect, the present disclosure relates to a process for preparing 3,7-bis(2-oxoindolin-3-ylidene)benzo[1,2-b:4,5-b']difuran-2,6-dione dicyanide and derivatives thereof. A general synthetic route for preparing 3,7-bis(2-oxoindolin-3-ylidene)benzo[1,2-b:4,5-b']difuran-2,6-dione dicyanide and derivatives thereof, in accordance with an embodiment of the present disclosure, is depicted in Scheme 1. A person skilled in the art would understand that all reaction conditions, including, for example, reactant(s), reaction solvent, reaction time, reaction temperature, reaction pressure, reactant ratio and whether or not the reaction should be performed under an anhydrous or inert atmosphere, can be varied to optimize the yield of the desired product(s) and it is within their skill to do so. An inert atmosphere includes, for example, under nitrogen or argon. Heating temperatures will vary depending on the reactants, however, will generally be about 50° C. to about 220° C., or about 70° C. to about 210° C. Reaction times will also vary depending on the reactants, but can be determined using methods known in the art, for example, by following the reaction progress by thin layer chromatography (TLC) or nuclear magnetic resonance (NMR) spectroscopy, and monitoring the disappearance of starting materials and/or formation of product. Reactions will be complete when a sufficient amount of the product is formed. Reaction solvents, temperatures and times are parameters that are readily selected by a person of skill in the art.

Scheme 1

*ALKYL HALIDE
**CYANATING REAGENT

In accordance with the embodiment depicted in Scheme 1, the 3,7-bis(2-oxoindolin-3-ylidene)benzo[1,2-b:4,5-b']difuran-2,6-dione dicyanide derivatives were prepared via a three-step reaction sequence using commercially available 6-bromoisatin as the starting material. In an embodiment, the reaction sequence was carried out using materials not requiring anhydrous and/or inert atmospheric conditions. The product yields obtained for each step were generally in excess of 50%. Various reagents and conditions appropriate for the conversion of 6-bromoisatin into the 6-cyanoisatin (*) are known to the skilled person. In an embodiment, the cyanation reaction was carried out in N-methyl-2-pyrrolidone (NMP) using commercially available CuCN. The resulting crude product was precipitated in water, collected by filtration, and further purified by silica gel column chromatography. The condensation reaction between 6-cyanoisatin and benzodifurandione proceeded readily in refluxing acetic acid in the presence of a catalytic amount of toluenesulfonic acid. Following cooling, the crude product was collected by filtration, and further purified by silica gel chromatography. It is important to note that when the cyanation reaction was carried out directly on 3,7-bis(2-oxoindolin-3-ylidene)benzo[1,2-b:4,5-b']difuran-2,6-dione dibromide, the benzodifurandione core was lost. Moreover, the condensation reaction was quite sensitive, considering the propensity of the cyano groups to hydrolysis under acidic conditions. The chemical structures of the dicyanide products were confirmed by $^1$H, $^{13}$C as well as by mass spectroscopy. The thermal properties of the dicyanide products were evaluated by thermal gravimetric analysis (TGA) and differential scanning calorimetry (DSC). The electrochemical properties of the dicyanide products were evaluated by cyclic voltammetry (CV). Finally, UV-Vis absorption spectra were recorded and optical bandgaps were calculated from the onset of the absorption band. The HOMO and LUMO energy levels were determined from the oxidation and reduction onsets from the CV spectra assuming the SCE electrode to be −4.7 eV from vacuum.

In an aspect, the present disclosure relates to organic electronics comprising 3,7-bis(2-oxoindolin-3-ylidene)benzo[1,2-b:4,5-b']difuran-2,6-dione dicyanide or derivatives thereof as the active materials. In an embodiment, the present disclosure relates to field-effect transistors and solar cells comprising 3,7-bis(2-oxoindolin-3-ylidene)benzo[1,2-b:4,5-b']difuran-2,6-dione dicyanide or derivatives thereof as the active materials.

Figure 1:
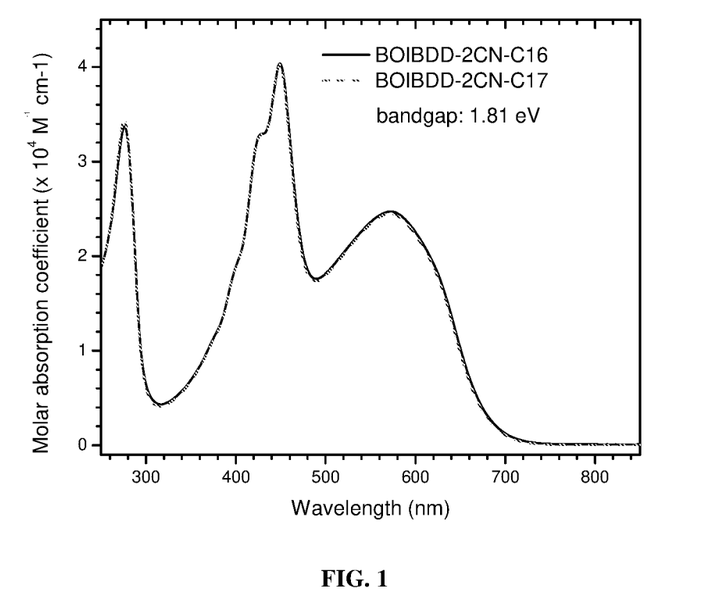
FIG. 1 is an illustration of the UV-Visible absorption spectra of BOIBDD-2CN—$C_{16}$ and BOIBDD-2CN—$C_{17}$ in solution in $CH_2Cl_2$, in accordance with an embodiment of the present disclosure.
Figure 2:
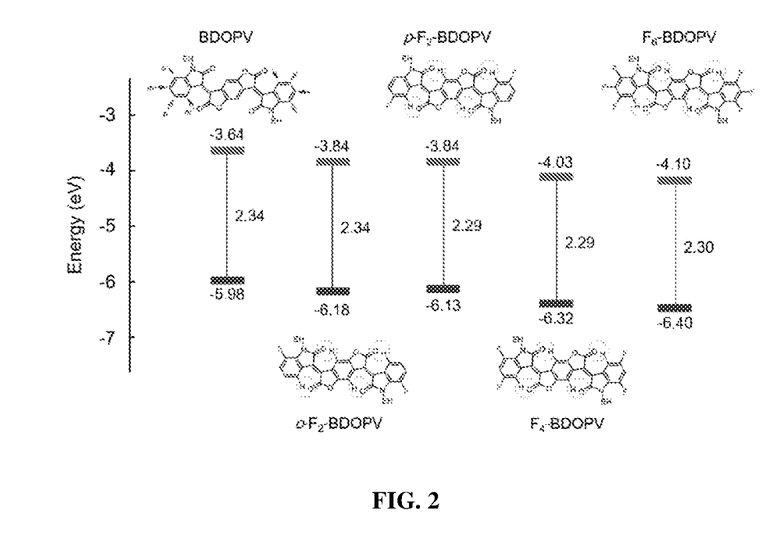
FIG. 2 is an illustration of the HOMO-LUMO energy levels of various fluorinated bis(2-oxoindolin-3-ylidene) benzodifurandione derivatives.

The optical bandgaps of BOIBDD-2CN—$C_{16}$ and BOIBDD-2CN—$C_{17}$ were found to be about 1.81 eV, based on their absorption onsets. This bandgap is smaller than those observed for fluorinated BOIBDD (~2.3 eV) implying that the cyano groups indeed increase the effective conjugation length (FIG. 2). It is worth noting that BOIBDD-2CN—$C_{16}$ absorbs very strongly in the visible region with molar absorption coefficients of 4.0×10$^4$ and 2.5×10$^4$ M$^{-1}$ cm$^{-1}$ at 449 and 573 nm, respectively (FIG. 1). These observations suggest that BOIBDD-2CN—$C_{16}$ and related materials can effectively function as n-type materials behaving as electron acceptors in organic solar cells. It is surmised that these n-type materials could replace the widely used fullerene derivatives such as PC$_{71}$BM because in organic solar cells because of their stronger absorption in the solar spectrum.

Figure 3:
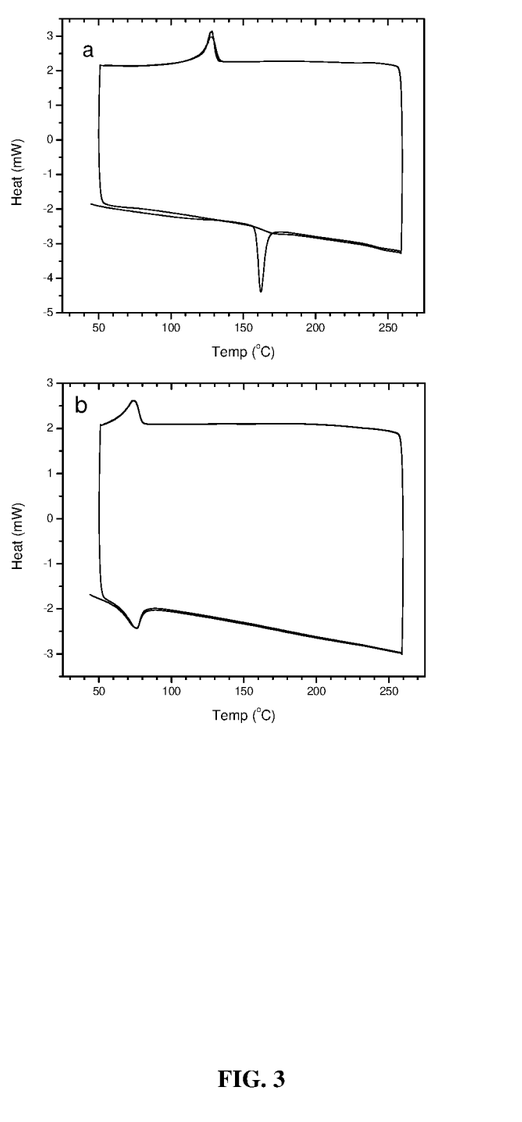
FIG. 3 is an illustration of the DSC thermograms obtained for: (a) BOIBDD-2CN—$C_{16}$ (second scan); and (b) BOIBDD-2CN—$C_{17}$, in accordance with an embodiment of the present disclosure.

In an aspect of the present disclosure, the thermal properties of this class of materials were investigated by DSC. In accordance with an embodiment of the present disclosure, the thermal properties of BOIBDD-2CN—$C_{16}$ ($C_{16}$ is 2-hexyldecyl) and BOIBDD-2CN—$C_{17}$ ($C_{17}$ is 3-hexylundecyl) were investigated by DSC. Even though structurally identical, with the exception of the side chains ($C_{16}$ vs $C_{17}$), the respective DSC thermograms exhibited surprising differences, indicative of the direct impact of the side chains on the thermal behavior of these materials (FIG. 3). It has been reported in the literature that side-chain structural modifications can improve the material's crystallinity and thus its electron mobility.[14-15] BOIBDD-2CN—$C_{16}$ did not exhibit any melting or crystallizing peaks up to 260° C. in the first DSC scan. A crystallizing and a melting peak, at 128° C. and 162° C. respectively, could be observed in the second DSC scan. However, BOIBDD-2CN—$C_{17}$ did exhibit a crystallizing and a melting peak at 74° C. and 76° C. respectively in the first DSC scan. Identical results were obtained in the second DSC scan. Considering that the BOIBDD backbone is quite large and rigid, it is surprising that BOIBDD-2CN—$C_{17}$ exhibits a melting peak as low as 76° C. This observation is further corroborated by the reported melting point of 255° C. for a BOIBDD core comprising a pair of $C_8$ (2-ethylhexyl) side chains.[8] Since the cyano groups can potentially increase the effective conjugation length of the BOIBDD core structure, it was surmised that BOIBDD-2CN should exhibit a higher melting point. Indeed, heating the samples to higher temperatures in DSC analysis revealed that BOIBDD-2CN—$C_{16}$ melts at 275° C. while BOIBDD-2CN—$C_{17}$ melts at a temperature as high as 305° C. Considering these results, it is speculated that the melting points of 76° C. and 162° C., as observed for BOIBDD-2CN—$C_{17}$ and BOIBDD-2CN—$C_{16}$ respectively, correspond to the melting process of the $C_{17}$ and $C_{16}$ side chains. The difference in observed melting points appears quite large, considering the relatively small structural difference in the respective side chains of BOIBDD-2CN—$C_{16}$ and BOIBDD-2CN—$C_{17}$. It is very likely that the $C_{16}$ and $C_{17}$ side chains cause these materials to adopt different crystalline structures and packing motifs, which could at least in part account for the better solubility of BOIBDD-2CN—$C_{17}$ in organic solvents as well BOIBDD-2CN—$C_{17}$ exhibiting better film-forming properties. Both materials are relatively stable, and the onset decomposition temperatures (1% weight loss) of BOIBDD-2CN—$C_{16}$ and BOIBDD-2CN—$C_{17}$ were found to be around 329° C. and 310° C., respectively.

Figure 4:
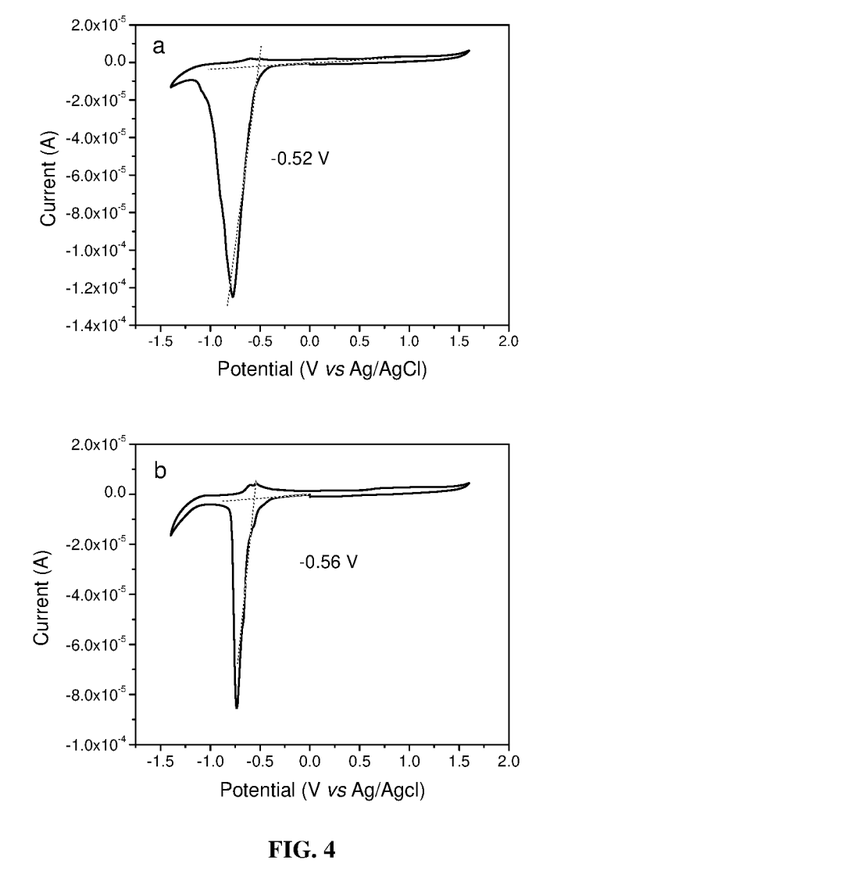
FIG. 4 is an illustration of the cyclic voltammograms obtained for: (a) BOIBDD-2CN—$C_{16}$ thin film cast from a $Bu_4NPF_6$/Acetonitrile solution at a scan rate of 50 mV/s; and (b) BOIBDD-2CN—$C_{17}$ thin film cast from a $Bu_4NPF_6$/Acetonitrile solution at a scan rate of 50 mV/s, in accordance with an embodiment of the present disclosure.

In an aspect of the present disclosure, the HOMO and LUMO energy levels of this class of materials were investigated by cyclic voltammetry (CV). In accordance with an embodiment of the present disclosure, the HOMO and LUMO energy levels of BOIBDD-2CN—$C_{16}$ ($C_{16}$ is 2-hexyldecyl) and BOIBDD-2CN—$C_{17}$ ($C_{17}$ is 3-hexylundecyl) were investigated by CV. The materials were dissolved in chloroform, followed by drop-casting the solution on a Pt electrode to generate a film. Both BOIBDD-2CN—$C_{16}$ and BOIBDD-2CN—$C_{17}$ were readily reduced during the cathodic reduction scan. As shown in FIG. 4, the reduction signals were very strong. Based on their onset reduction potentials, the LUMO energy levels of BOIBDD-2CN—$C_{16}$ and BOIBDD-2CN—$C_{17}$ were estimated to be around −4.25 and −4.21 eV, respectively. These values are about 0.25 eV lower than that observed for unsubstituted BOIBDD, suggesting that the cyano group is a strong electron withdrawing group and indeed effectively lowers the LUMO energy level. Oxidation peaks could not be observed during the CV measurements, indicating that hole injection into this class of materials is difficult and implying that these materials are unipolar n-type materials. The HOMO energy levels were estimated from their LUMO energy levels and optical band gaps to be around 6.06 and 6.02 eV for BOIBDD-2CN—$C_{16}$ and BOIBDD-2CN—$C_{17}$, respectively.

Figure 5:
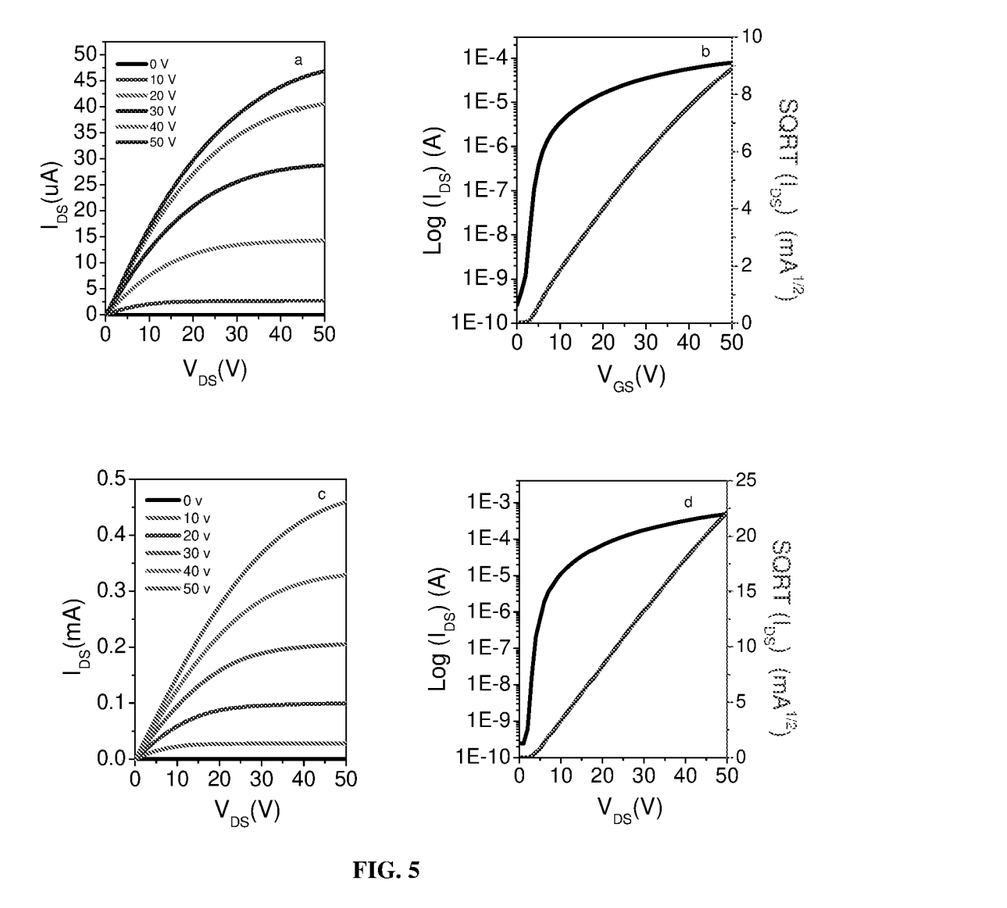
FIG. 5 is an illustration of the output and transfer characteristics for: (a, b) a transistor comprising a BOIBDD-2CN—$C_{16}$ active layer; and (c, d) a transistor comprising a BOIBDD-2CN—$C_{17}$ active layer, in accordance with an embodiment of the present disclosure.

In an aspect of the present disclosure, the electron mobility of this class of materials was investigated. In accordance with an embodiment of the present disclosure, the electron mobility of BOIBDD-2CN—$C_{16}$ ($C_{16}$ is 2-hexyldecyl) and BOIBDD-2CN—$C_{17}$ ($C_{17}$ is 3-hexylundecyl) were investigated by fabricating bottom-contact bottom-gated transistors on Fraunhofer pre-patterned substrates. The channel width was fixed at 10 mm, and the channel lengths varied from 20 μm to 2.5 μm (e.g. 20 μm, 10 μm, 5 μm, and 2.5 μm). In a particular embodiment of the present disclosure, a transistor having a channel length of 20 μm was manufactured. Prior to the device fabrication, the substrates (Si/$SiO_2$ substrate glass slides) were sonicated in acetone and 2-propanol and then exposed to air plasma at a power of 50 W over a period of 60 s. Immediately following plasma treatment, the SiO2 surface was passivated overnight with a solution of dodecyltrichlorosilane (DTS) in anhydrous toluene. The substrates were then rinsed with anhydrous toluene (3×) and dried on hot plates at 120° C. Bis(2-oxoindolin-3-ylidene)benzodifurandione dicyanide derivatives (e.g. BOIBDD-2CN—$C_{16}$ ($C_{16}$ is 2-hexyldecyl) and BOIBDD-2CN—$C_{17}$ ($C_{17}$ is 3-hexylundecyl)) were dissolved in anhydrous chloroform at a concentration of about 6 mg/ml. The resulting solutions were subsequently filtered inside a glove-box using a polytetrafluoroethylene (PTFE) filter (1 μm) and deposited by spin-coating. The spin-coated films were then annealed at 130° C. (for BOIBDD-2CN—$C_{16}$) and 75° C. (for BOIBDD-2CN—$C_{17}$) in the glove box filled with nitrogen for 24 hours, followed by slow cooling to room temperature. The output and transfer characteristics of the fabricated transistors were subsequently measured in air and under a stream of nitrogen using a Keithley 4200 Semiconductor Analyzer. The field-effect mobility was extracted from the transfer curves obtained using the standard transistor current voltage equation in the saturation regime. Both BOIBDD-2CN—$C_{16}$ and BOIBDD-2CN—$C_{17}$ exhibited unipolar electron transport. Based on 10 devices, the average electron mobility for a device comprising BOIBDD-2CN—$C_{16}$ and a device comprising BOIBDD-2CN—$C_{17}$ was about 0.01 and 0.09 $cm^2$/Vs, respectively. The output and transfer characteristics of the transistors are illustrated in FIG. 5. As shown in FIG. 5, the on/off ratios are above $10^5$ for both materials and the threshold voltages are below 4V, indicating low electron injection barriers even when using high-work function Au electrodes. In an embodiment of the present disclosure, the transistors are air stable, even without any encapsulation. To that effect, the transistor comprising BOIBDD-2CN—$C_{17}$ as the active layer was shown to exhibit an electron mobility of about 0.085 $cm^2$/Vs following three (3) days of exposure to air. The observed stability was significantly better that that observed for commercially available high mobility n-type polymer P(NDI2OD-T2). Indeed, in bottom-contact and bottom-gated transistors, the performance of P(NDI2OD-T2) degraded within one hour of air exposure.

Experimental

General: $^1$H spectra were recorded on a Varian AS400 spectrometer in deuterated solvents. Chemical shifts (δ) are reported in parts per million (ppm) relative to the residual protic solvent. UV-Vis absorption spectra were recorded using a Thermo Scientific Genesys 10S spectrophotometer using 1 cm path-length quartz cells. Optical bandgaps were calculated from the onset of the absorption band. Cyclic voltammograms (CV) were recorded on a CHI600E electrochemical analyser using a pair of platinum disks as the working electrode and counter-electrode, at a scan rate of 50 mV/s, and an Ag/$Ag^+$ reference electrode (0.01 M of $AgNO_3$ in acetonitrile) in an anhydrous and argon-saturated solution of 0.1 M tetrabutylammonium hexafluorophosphate ($Bu_4NPF_6$) in anhydrous acetonitrile (electrolyte). Under these conditions, the onset reduction potential ($E^{red}$) of ferrocene was 0.03V versus Ag/$Ag^+$. Ferrocene, used as the reference, has a HOMO energy level of −4.7 eV. The LUMO and HOMO energy levels of the materials were determined using the empirical equations, $E_{LUMO} = -(E^{red}_{onset} + 4.77)$ eV and $E_{HOMO} = -(E^{ox}_{onset} + 4.77)$ eV, respectively, where $E^{ox}_{onset}$ and $E^{red}_{onset}$ are the onset potentials for oxidation and reduction relative to the Ag/$Ag^+$ electrode, respectively. Thermogravimetric analysis (TGA) measurements were carried out using a Mettler Toledo TGA SDTA 851e apparatus at a heating rate of 10° C./min under a nitrogen atmosphere. The temperature of onset degradation ($T_d$) corresponds to a 1% weight loss. Differential scanning calorimetric (DSC) analyses was performed using a Perkin-Elmer DSC-7 instrument, calibrated with ultra-pure indium at a scanning rate of 10° C./min under a nitrogen atmosphere.

Materials: Unless otherwise noted, starting materials, reactants and solvents were obtained commercially and were used as such or purified by standard means.

A number of non-limiting examples are provided in the following sections, illustrating the preparation of bis(2-oxoindolin-3-ylidene)benzodifurandione dicyanide or derivatives thereof in accordance with various embodiments of the present disclosure. The following non-limiting examples are illustrative of the present disclosure.

General Procedure for the Alkylation of 6-Bromoisatin

To a 3-necked flask (100 ml) equipped with a condenser were added 6-bromoisatin (0,678 g, 3 mmol) and $K_2CO_3$ (0.828 g, 6 mmol). The system was then purged several times with Ar (e.g. 3 times). Alkyl halide (e.g. an alkyl iodide) in anhydrous DMF (20 mL) was subsequently added via a syringe. The reaction mixture was then stirred while at 70° C. under Ar for period of about 15 hrs. Following cooling, the solvents were removed by vacuum distillation and the resulting residue redissolved in chloroform (50 mL). The resulting chloroform solution was filtered to remove any insoluble residue and concentrated to yield a brown oil. The crude product was purified by silica gel chromatography using dichloromethane as the eluent. The purified product solidified overnight.

Alkyl halide is 2-hexyldecyliodide: $^1$H NMR 400 MHz ($C_6D_6$) δ (ppm): 6.78 (d, J=8.0 Hz, 1H), 6.65 (d, J=1.2 Hz, 1H), 6.58 (dd, $J_1$=8 Hz, $J_2$=1.2 Hz, 1H), 3.11 (d, J=7.6 Hz, 2H), 1.62 (m, 1H), 1.40-1.10 (m, 24H), 0.94-0.87 (m, 6H). Yield 69.9% (0.945 g).

Alkyl halide is 3-hexylundecyliodide: $^1$H NMR 400 MHz ($C_6D_6$) δ (ppm): 6.79 (d, J=8.0 Hz, 1H), 6.60 (dd, $J_1$=8.0 Hz, $J_2$=1.6 Hz, 1H), 6.56 (d, J=1.6 Hz, 1H), 3.18 (t, J=7.6 Hz, 1H), 1.40-1.10 (m, 27H), 0.96-0.89 (m, 6H). Yield 74.6% (1.04 g).

General Procedure for the Preparation of 1-Alkyl-6-Cyanoisatins

In an oven-dried one-necked flask (50 ml) were added 1-alkyl-6-bromoisatin (2 mmol), CuCN (0.36 g, 4 mmol), and NMP (10 mL). The system was then purged several times with Ar (e.g. 3 times) followed by heating the reaction mixture at 204° C. using a salt bath while under Ar for period of about 4 hrs. Following cooling to 150° C., the reaction mixture was poured into an aqueous $FeCl_3$ solution (2.0 g of $FeCl_3$ dissolved in 2M HCl (15 mL). After stirring for 10 min, the reaction mixture was extracted using chloroform (50 mL). The organic phase was subsequently washed with a 2M HCl solution (2×15 mL) and water, dried over $MgSO_4$ and concentrated under vacuum. The crude product was purified by silica gel chromatography using dichloromethane as the eluent. The purified product solidified overnight.

Alkyl is 2-hexyldecyl: $^1$H NMR 400 MHz ($C_6D_6$) δ (ppm): 6.71 (d, J=7.6 Hz, 1H), 6.42 (d, J=1.2 Hz, 1H), 6.34 (dd, $J_1$=7.6 Hz, $J_2$=1.2 Hz, 1H), 3.09 (d, J=7.6 Hz, 2H), 1.57 (m, 1H), 1.40-1.10 (m, 24H), 0.94-0.87 (m, 6H). Yield 62.0% (0.492 g).

Alkyl is 3-hexylundecyl: $^1$H NMR 400 MHz ($C_6D_6$) δ (ppm): 6.70 (d, J=7.6 Hz, 1H), 6.34 (dd, $J_1$=7.6 Hz, $J_2$=0.8 Hz, 1H), 6.30 (d, J=0.8 Hz, 1H), 3.15 (t, J=7.2 Hz, 2H), 1.40-1.15 (m, 27H), 0.96-0.89 (m, 6H). Yield 62.3% (0.511 g).

General Procedure for the Preparation of bis(2-oxoindolin-3-ylidene)benzodifurandione Dicyanide or Derivatives Thereof In an oven-dried one-necked flask (100 ml) were added 1-alkyl-6-cyanoisatin (1.3 mmol), benzodifurandione (0.54 mmol), toluenesulfonic acid (25 mL) and glacial acetic acid (30 mL). The reaction mixture was then stirred while at 115° C. under $N_2$ for period of about 18 hrs. Following cooling, the crude product was collected by filtration and washed with acetic acid and methanol. The crude product was further purified by silica gel chromatography using hexanes/dichloromethane (1:4) as the eluent.

Alkyl is 2-hexyldecyl: $^1$H NMR 400 MHz ($C_6D_6$) δ (ppm): 9.39 (s, 2H), 9.04 (d, J=8.0 Hz, 2H), 6.76 (dd, $J_1$=8.4 Hz, $J_2$=1.6 Hz, 2H), 6.62 (d, J=1.6 Hz, 2H), 3.33 (d, J=7.6 Hz, 2H), 1.45-1.20 (m, 48H), 0.98-0.88 (m, 12H). Yield 38.6% (0.197 g).

Alkyl is 3-hexylundecyl: $^1$H NMR 400 MHz ($C_6D_6$) δ (ppm): 9.40 (s, 2H), 9.03 (d, J=8.4 Hz, 2H), 6.76 (dd, $J_1$=8.4 Hz, $J_2$=1.6 Hz, 2H), 6.53 (d, J=1.6 Hz, 2H), 3.41 (d, J=7.6 Hz, 2H), 1.45-1.25 (m, 54H), 1.00-0.90 (m, 12H). Yield 38.3% (0.203 g).

While the present disclosure has been described with reference to specific examples, it is to be understood that the disclosure is not limited to the disclosed examples. To the contrary, the disclosure is intended to cover various modifications and equivalent arrangements included within the spirit and scope of the appended claims.

All publications, patents and patent applications cited in the present disclosure are herein incorporated by reference in their entirety to the same extent as if each individual publication, patent or patent application was specifically and individually indicated to be incorporated by reference in its entirety.

REFERENCES

1. I. Kang, H. Yun, D. Chung, S. Kwon, Y. Kim, J. Am. Chem. Soc. 2013, 135, 14896.
2. Y. Li, P. Sonar, L. Murphya, W. Honga, Energy Environ. Sci. 2013, 6, 1684.
3. H. Tseng, H. Phan, C. Luo, M. Wang, L. A. Perez, S. N. Patel, L. Ying, E. J. Kramer, T. Nguyen, G. C. Bazan, A. J. Heeger, Adv. Mater. 2014, 26, 2993.
4. Y. Yuan, G. Gir, A. L. Ayzner, A. P. Zoombelt, S. C. B. Mannsfeld, J. Chen, D. Nordlund, M. F. Toney, J. Huang, Z. Bao, Nature Commun. 2014, 5, 3005.
5. J. Li, Y. Zhao, H. Tan, Y. Guo, C. Di, G. Yu, Y. Liu, M. Lin, S. Lim, Y. Zhou, H, Su, B. Ong, Sci. Rep. 2012, 2, 754.
6. X. Zhan, A. Facchetti, S. Barlow, T. J. Marks, M. A. Ratner, M. R. Wasielewski, S. R. Marder, Adv. Mater. 2011, 23, 268.
7. T. Lei, X. Xia, J. Wang, C. Liu, J. Pei, J. Am. Chem. Soc. 2014, 136, 2135.
8. J. Dou, Y. Zheng, Z. Yao, Z. Yu, T. Lei, X. Shen, X. Luo, J. Sun, S. Zhang, Y. Ding, G. Han, Y. Yi, J. Wang, J. Pei, J. Am. Chem. Soc. 2015, 137, 15947.
9. F. Zhang, Y. Hu, T. Schuettfort, C. Di, X. Gao, C. McNeill, L. Thomsen, S. Mannsfeld, W. Yuan, H. Sirringhaus, D. Zhu, J. Am. Chem. Soc. 2013, 135, 2338.
10. WO 2014/071524 A1.
11. H.-Y. Chen, J. Hou, S. Zhang, Y. Liang, G. Yang, Y. Yang, L. Yu, Y. Wu and G. Li, Nature Photon., 2009, 3, 649.
12. Z. Li, J. Lu, S. Tse, J. Zhou, X. Du, Y. Tao, J. Ding, J. Mater. Chem., 2011, 21, 3226-3233.
13. S. Alem, S. Wakim, J. Lu, G. Robertson, J. Ding, Y. Tao, ACS Appl. Mater. Interfaces, 2012, 4, 2993-2998.
14. T. Lei, J. Dou, J. Pei, Adv. Mater. 2012, 24, 6457.
15. J. Mei, D. H. Kim, A. L. Ayzner, M. F. Toney, Z. Bao, et al, J. Am. Chem. Soc. 2011, 133, 20130.

The invention claimed is:

1. A bis(2-oxoindolin-3-ylidene)benzodifurandione dicyanide or a derivative thereof consisting of formula (I):

(I)

wherein
X and Y are independently selected from H and F; and
R is $C_{11-40}$alkyl, fluorinated $C_{1-40}$alkyl, $C_{2-40}$alkenyl, fluorinated $C_{2-40}$alkenyl, $C_{2-40}$alkynyl, fluorinated $C_{2-40}$alkynyl, $C_{5-40}$aryl, or $C_{5-40}$heteroaryl.

2. The bis(2-oxoindolin-3-ylidene)benzodifurandione dicyanide or derivative thereof as defined in claim 1 consisting of the structure:

3. The bis(2-oxoindolin-3-ylidene)benzodifurandione dicyanide or derivative thereof as defined in any one of claim 1 consisting of the structure:

4. An organic semiconductor material, layer or component comprising the bis(2-oxoindolin-3-ylidene)benzodifurandione dicyanide or derivative thereof as defined in claim 1.

5. The organic semiconductor material, layer or component as defined in claim 4, wherein the semiconductor material, layer or component is an n-type semiconductor material, layer or component.

6. An electronic device comprising the bis(2-oxoindolin-3-ylidene)benzodifurandione dicyanide or derivative thereof as defined claim 1.

7. The electronic device as defined in claim 6, wherein the device is an organic photovoltaic device, a photodiode or an organic filed effect transistor.

8. Use of the bis(2-oxoindolin-3-ylidene)benzodifurandione dicyanide or derivative thereof as defined in claim 1 as an organic semiconductor material, layer or component.

9. Use of the bis(2-oxoindolin-3-ylidene)benzodifurandione dicyanide or derivative thereof as defined in claims 1 in an electronic device.

10. The use according to claim 9, wherein the device is an organic photovoltaic device, a photodiode or an organic filed effect transistor.

11. The bis(2-oxoindolin-3-ylidene)benzodifurandione dicyanide or a derivative thereof as defined in claim 1, characterized by LUMO energy levels at or below −4.10 eV.

12. A formulation comprising the bis(2-oxoindolin-3-ylidene)benzodifurandione dicyanide and/or a derivative thereof as defined in claim 1, and an organic solvent.

13. A bis(2-oxoindolin-3-ylidene)benzodifurandione dicyanide or a derivative thereof consisting of formula (I):

(I)

wherein
X and Y are independently selected from H and F; and
R is $C_{11-40}$alkyl.

14. A bis(2-oxoindolin-3-ylidene)benzodifurandione dicyanide or a derivative thereof consisting of formula (I):

(I)

wherein
X and Y are H; and
R is $C_{11-40}$alkyl.

* * * * *